US007186277B2

(12) United States Patent
Genet et al.

(10) Patent No.: US 7,186,277 B2
(45) Date of Patent: Mar. 6, 2007

(54) COMPOSITION FOR DYEING KERATIN FIBRES, COMPRISING A CATIONIC PARA-PHENYLENEDIAMINE DERIVATIVE SUBSTITUTED WITH A DIAZACYCLOHEXANE OR DIAZACYCLOHEPTANE RING

(75) Inventors: Alain Genet, Aulnay Sous Bois (FR); Stéphane Sabelle, Paris (FR)

(73) Assignee: L'Oreal SA, Paris (FR)

( * ) Notice: Subject to any disclaimer, the term of this patent is extended or adjusted under 35 U.S.C. 154(b) by 289 days.

(21) Appl. No.: 10/807,167

(22) Filed: Mar. 24, 2004

(65) Prior Publication Data
US 2004/0237216 A1 Dec. 2, 2004

Related U.S. Application Data

(60) Provisional application No. 60/506,766, filed on Sep. 30, 2003.

(30) Foreign Application Priority Data
Mar. 24, 2003  (FR) .................... 03 03547

(51) Int. Cl.
*A61K 7/13* (2006.01)
(52) U.S. Cl. .................. 8/405; 8/406; 8/410; 8/411; 8/421; 8/567; 8/573; 8/602; 8/606; 540/575; 544/394; 514/341
(58) Field of Classification Search .............. 8/405, 8/406, 410, 411, 421, 567, 573, 602, 606; 540/575; 544/394; 514/341
See application file for complete search history.

(56) References Cited

U.S. PATENT DOCUMENTS

| | | | | |
|---|---|---|---|---|
| 4,003,699 A | 1/1977 | Rose et al. | ..................... | 8/10.2 |
| 4,745,652 A | 5/1988 | Rose et al. | ..................... | 8/409 |
| 4,823,985 A | 4/1989 | Grollier et al. | ................. | 222/1 |
| 5,061,289 A | 10/1991 | Clausen et al. | ................ | 8/405 |
| 5,380,340 A | 1/1995 | Neunhoeffer et al. | .......... | 8/409 |
| 5,534,267 A | 7/1996 | Neunhoeffer et al. | ........ | 424/701 |
| 5,663,366 A | 9/1997 | Neunhoeffer et al. | .... | 548/371.4 |
| 5,766,576 A | 6/1998 | Löwe et al. | ................... | 424/62 |
| 6,099,592 A | 8/2000 | Vidal et al. | ..................... | 8/409 |
| 6,165,230 A | 12/2000 | Rose et al. | ..................... | 8/409 |
| 6,240,929 B1 | 6/2001 | Richard et al. | | |
| 6,284,003 B1 | 9/2001 | Rose et al. | ..................... | 8/412 |
| 6,338,741 B1 | 1/2002 | Vidal et al. | ..................... | 8/409 |
| 6,565,614 B1 | 5/2003 | Genet et al. | .................... | 8/406 |
| 6,638,321 B1 | 10/2003 | Genet et al. | .................... | 8/407 |
| 2003/0199642 A1 | 10/2003 | Schneider et al. | | |

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| DE | 197 07 545 | 8/1998 |
| EP | 0 327 763 | 8/1989 |
| EP | 0 770 375 B1 | 5/1997 |
| FR | 2 288 093 | 5/1975 |
| FR | 2 586 913 A1 | 3/1987 |
| FR | 2 733 749 A1 | 11/1996 |
| FR | 2 828 488 | 2/2003 |
| JP | 63-51378 | 3/1988 |
| JP | 2-19576 | 1/1990 |
| JP | A-H10-87946 | 4/1998 |
| JP | 2000-503036 | 3/2000 |
| JP | 2000-503037 | 3/2000 |
| JP | 2000-119231 A | 4/2000 |
| JP | T-2000-513409 | 10/2000 |
| JP | T-2003-530414 | 10/2003 |
| JP | T-2004-506669 | 3/2004 |
| JP | A-2004-525147 | 8/2004 |
| WO | WO 94/08969 | 4/1994 |
| WO | WO 94/08970 | 4/1994 |
| WO | WO 96/15765 | 5/1996 |
| WO | WO 99/03819 | 1/1999 |
| WO | WO 99/03836 | 1/1999 |
| WO | WO 99/50338 | 10/1999 |
| WO | WO 01/78664 A1 | 10/2001 |
| WO | WO 02/078655 A2 | 10/2002 |
| WO | WO 02/102250 | 12/2002 |
| WO | WO 03/014093 | 2/2003 |

OTHER PUBLICATIONS

Romanelli et al. J. Med. Chem. 2001, 44, 3946-3955.*
STIC Search Report Mar. 23, 2006.*
English language Derwent Abstract of FR 2 288 093, May 14, 1975.
English language Derwent Abstract of FR 2 828 488, Feb. 14, 2003.
English language Derwent Abstract of EP 0 770 375, May 2, 1997.
English language Derwent Abstract of JP 2-19576, Jan. 23, 1990.
English language Derwent Abstract of JP 2000-119231 A, Apr. 25, 2000.
English language abstract of JP-A-H10-87946.

* cited by examiner

*Primary Examiner*—Eisa Elhilo
(74) *Attorney, Agent, or Firm*—Finnegan Henderson Farabow Garrett & Dunner LLP

(57) ABSTRACT

In one embodiment, the disclosure relates to a composition for dyeing keratin fibres, for example, human keratin fibres such as the hair, comprising at least one para-phenylenediamine derivative substituted with a diazacyclohexane or diazacycloheptane ring, the nitrogen in position 4 of which is a quaternary ammonium. The present disclosure may make it possible, for example, to obtain at least one of chromatic, strong, relatively unselective, fast coloration of keratin fibres.

28 Claims, No Drawings

COMPOSITION FOR DYEING KERATIN FIBRES, COMPRISING A CATIONIC PARA-PHENYLENEDIAMINE DERIVATIVE SUBSTITUTED WITH A DIAZACYCLOHEXANE OR DIAZACYCLOHEPTANE RING

This application claims benefit of U.S. Provisional Application No. 60/506,766, filed Sep. 30, 2003.

In one embodiment, the disclosure relates to a composition for dyeing keratin fibres, for example, human keratin fibres such as the hair, comprising as an oxidation base at least one para-phenylenediamine derivative substituted with a diazacyclohexane or diazacycloheptane ring, the nitrogen in position 4 of which is a quaternary ammonium.

It is known practice to dye keratin fibres, for example, human keratin fibres such as the hair with dye compositions comprising oxidation dye precursors, generally known as oxidation bases, for example, ortho- or para-phenylenediamines; ortho- or para-aminophenols; heterocyclic compounds such as diaminopyrazole derivatives; pyrazolo[1,5-a]pyrimidine derivatives; pyrimidine derivatives; pyridine derivatives; 5,6-dihydroxyindole derivatives and 5,6-dihydroxyindoline derivatives. Oxidation dye precursors, or oxidation bases, are colourless or weakly coloured compounds that, when combined with oxidizing products, can give rise to coloured compounds or dyes by a process of oxidative condensation.

It is also known that the shades obtained with these oxidation bases may be varied by combining them with couplers or coloration modifiers, the latter being chosen, for example, from meta-phenylenediamines, meta-aminophenols, meta-hydroxyphenols and certain heterocyclic compounds such as, for example, pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules used as oxidation bases and couplers allows a wide range of colours to be obtained.

In one embodiment, the "permanent" coloration obtained with these oxidation dyes may moreover satisfy a certain number of requirements. It may have no toxicological drawbacks, it may allow shades to be obtained in the desired intensity, and it may show good resistance to external agents such as light, bad weather, washing, permanent-waving, perspiration and rubbing.

The dyes may also allow white hairs to be covered and, finally, they may be as unselective as possible, i.e. they may produce the smallest possible colour differences along the same length of keratin fibre, which may in fact be differently sensitized (i.e. damaged) between its end and its root. They may also show good chemical stability in the formulations, and may have a good toxicological profile.

In the field of hair dyeing, para-phenylenediamine and para-tolylenediamine are oxidation bases that are widely used. They can give varied shades with oxidation couplers.

However, for some embodiments, it is desirable to discover novel oxidation bases that have a better toxicological profile than para-phenylenediamine and para-tolylenediamine, while at the same time giving the hair excellent properties in terms of colour intensity, variety of shades, colour uniformity and fastness with respect to external agents.

It is already known practice to use 1,4-diazacycloheptane derivatives for the oxidation dyeing of keratin fibres. For example, U.S. Pat. No. 6,165,230 describes a dye composition comprising 1,4-diazacycloheptane derivatives substituted on the two nitrogen atoms of the ring with a 4'-aminobenzene group.

It has already been proposed, for example, in patents FR 9 709 027 and FR 9 709 028, to use para-pheylenediamine derivatives comprising a cationic group.

In some embodiments, however, these compounds may not make it possible to give a coloration that is equivalent in quality to that obtained with para-phenylenediamine or with para-tolylenediamine due to the lack of intensity and colour uniformity.

Thus, it is still desirable for some uses to discover novel oxidation bases that have both a good toxicological profile and properties such that the dye compositions containing them are able to give the hair excellent properties in terms of colour intensity, variety of shades, colour uniformity and fastness with respect to the various external attacking factors to which the hair may be subjected.

One of the objectives of the present disclosure is to develop novel dye compositions that may not have the drawbacks of the oxidation bases of the prior art, by providing novel dye compositions for dyeing keratin fibres, which do not degrade the keratin fibres, while at the same time being capable of generating intense colorations in varied shades, which are relatively unselective, resistant and have a good toxicological profile.

This objective may be achieved by the present disclosure, one non-limiting embodiment of which is a composition for dyeing keratin fibres, for example, human keratin fibres such as the hair, comprising, in a cosmetic medium that is suitable for dyeing, at least one para-phenylenediamine derivative of formula (I), as used herein formula (I) refers to formula (Ia), formula (Ib), and their addition salts:

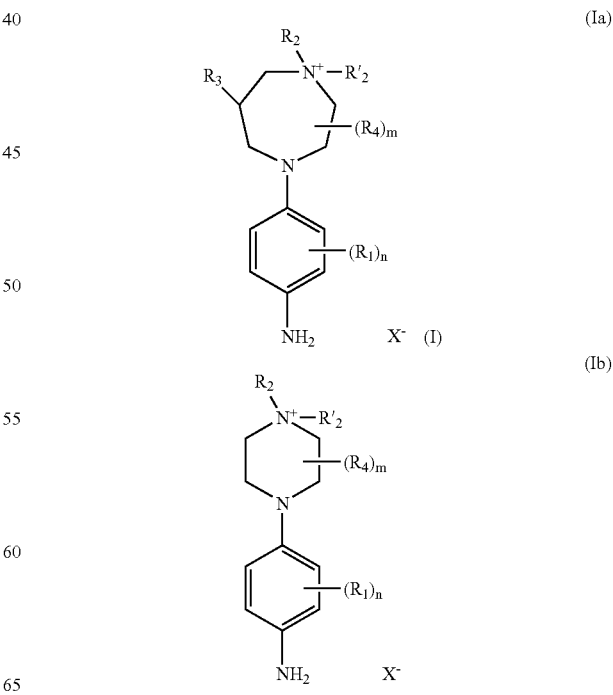

wherein:
R₁ is chosen from:
a halogen atom; and
saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;
n ranges from 0 to 4, wherein, when n is greater than 1, each $R_1$ may be identical or different;
$R_2$ and $R'_2$, which may be identical or different, are chosen from:
saturated and unsaturated alkyl radicals, wherein saturated and unsaturated alkyl radicals may be optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —CH₂R radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;
aryl radicals; and
benzyl radicals;
$R_3$ is chosen from:
a hydrogen atom;
optionally unsaturated alkyl radicals;
hydroxyl radicals;
hydroxyalkyl radicals;
alkoxy radicals;
alkoxyalkyl radicals;
alkylcarbonyl radicals;
hydroxyalkoxyalkyl radicals;
amino radicals, wherein the amine is optionally monosubstituted or disubstituted with a radical chosen from alkyl radicals, acetyl radicals and hydroxyalkyl radicals;
alkyl radicals substituted with at least one hydroxy radical and at least one amino radical;
monoalkylamino radicals;
dialkylamino radicals;
aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion.

The present disclosure makes it possible, for example, to obtain at least one of chromatic, strong, relatively unselective and fast dyeing of keratin fibres.

Another subject of the disclosure is a process for dyeing keratin fibres using the composition disclosed herein.

Other non-limiting embodiments of the disclosure are novel para-phenylenediamine derivatives substituted with at least one ring chosen from diazacyclohexane and diazacycloheptane, the nitrogen in position 4 of which is a quaternary ammonium.

Another non-limiting embodiment of the invention is a para-nitroaniline derivative substituted with at least one ring chosen from diazacyclohexane and diazacycloheptane, the nitrogen in position 4 of which is a quaternary ammonium, allowing the synthesis of the derivatives of formula (I) described above.

The compounds of formula (I) are para-phenylenediamines wherein one amine is included in a ring chosen from the 1,4-diazacycloheptane type, known in the literature as 1,4-diazepane; and the 1,4-diazacyclohexane type, known in the literature as 1,4-piperazine.

In the above definitions, the alkyl radicals are linear or branched and, unless otherwise mentioned, comprise from 1 to 10 carbon atoms, for example, from 1 to 6 carbon atoms. An alkoxy radical is an alkyl-O-radical, the alkyl radical being as defined above.

The expression "unsaturated alkyl radical" means an alkyl ranging from 2 to 10 carbon atoms comprising at least one double and/or triple bonds. A substituted alkyl radical is a monosubstituted or polysubstituted alkyl. For example, a hydroxyalkyl or an aminoalkyl is an alkyl that may be substituted with at least one hydroxyl or amino group, respectively.

In formula (I), the radical $R_1$ may be chosen, for example, from chlorine atoms, methyl radicals, ethyl radicals, isopropyl radicals, vinyl radicals, allyl radicals, methoxymethyl radicals, hydroxymethyl radicals, 1-carboxymethyl radicals, 1-aminomethyl radicals, 2-carboxyethyl radicals, 2-hydroxyethyl radicals, 3-hydroxypropyl radicals, 1,2-dihydroxyethyl radicals, 1-hydroxy-2-aminoethyl radicals, 1-amino-2-hydroxyethyl radicals, 1,2-diaminoethyl radicals, methoxy radicals, ethoxy radicals, allyloxy radicals, and 2-hydroxyethyloxy radicals.

According to one non-limiting embodiment of the invention, n is equal to 0 or $R_1$ is chosen from alkyl radicals, hydroxyalkyl radicals, aminoalkyl radicals, alkoxy radicals, and hydroxyalkoxy radicals. In the latter case, when n is not equal to 0, the radical $R_1$ may, for example, be chosen from methyl radicals, hydroxymethyl radicals, 2-hydroxyethyl radicals, 1,2-dihydroxyethyl radicals, methoxy radicals, isopropyloxy radicals, and 2-hydroxyethoxy radicals, for instance, methyl radicals, hydroxymethyl radicals, and 1,2-dihydroxyethyl radicals.

According to one non-limiting embodiment of the invention, the oxidation bases of formula (I) are such that n is equal to 0 or 1.

According to another non-limiting embodiment of the disclosure, the radical $R_2$ is chosen from an alkyl radical; an alkyl radical substituted with a saturated or unsaturated heterocyclic radical comprising 4, 5, 6 or 7 atoms, at least one hetero atom of which is chosen from nitrogen, oxygen, sulphur, and —$CH_2R$ radicals, wherein R is an alkyl radical substituted with at least one hydroxyl radical. A substituted alkyl radical, as used in this disclosure, may be saturated or unsaturated. In this case, the radical $R_2$, for example, may be chosen from a 2-hydroxyethyl radical, a 2,3-dihydroxypropyl radical, a 3-(1-pyrrolidinyl)propyl radical, and a methyl radical. For example, the radical $R_2$ may be chosen from a 2-hydroxyethyl radical and a methyl radical.

According to one non-limiting embodiment of the disclosure, the radical $R'_2$ is chosen from alkyl radicals and —$CH_2R$ radicals, wherein R is an alkyl radical substituted with at least one radical chosen from hydroxyls, aminos, monoalkylaminos and dialkylaminos. In this case, the radical $R'_2$ may be, for example, chosen from a methyl radical, an ethyl radical, and a 2-hydroxyethyl radical.

According to one non-limiting embodiment of the disclosure, the radical $R_3$ is chosen from a hydrogen atom, alkyl radicals, hydroxyalkyl radicals, aminoalkyl radicals, carboxyl radicals, carbamoyl radicals, hydroxyl radicals, alkoxy radicals, amino radicals, monoalkylamino radicals, and dialkylamino radicals. In this case, the radical $R_3$ may be chosen from, for example, a hydrogen atom, a hydroxyl radical, a carboxyl radical, a carbamoyl radical, an amino radical, a hydroxymethyl radical, and an aminomethyl radical. For instance, the radical $R_3$ is a hydrogen atom.

According to one non-limiting embodiment of the disclosure, m is equal to 0 or $R_4$ is chosen from alkyl radicals, hydroxyalkyl radicals, aminoalkyl radicals, carboxyl radicals, carbamoyl radicals, monoalkylcarbamoyl radicals, and dialkylcarbamoyl radicals. For example, m is equal to 0 or 1.

The compounds of formula (I) may optionally be salified with strong mineral acids, for instance, HCl, HBr and $H_2SO_4$, or organic acids, for instance acetic acid, lactic acid, tartaric acid, citric acid and succinic acid.

The counterion ($X^-$) disclosed herein may be chosen from halide ions such as chloride, bromide, fluoride and iodide ions; hydroxide ions; hydrogen sulphate ions; and $C_1$–$C_6$ alkyl sulphate ions such as methyl sulphate and ethyl sulphate.

Examples of the derivatives of formula (I) that may be mentioned include the compounds given in the table below.

| Formula | Nomenclature |
| --- | --- |
| 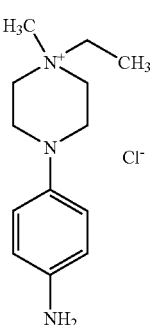 | 4-(4-aminophenyl)-1-ethyl-1-methylpiperazin-1-ium chloride |
| 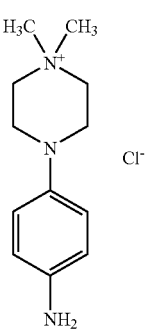 | 4-(4-aminophenyl)-1,1-dimethylpiperazin-1-ium chloride |
| 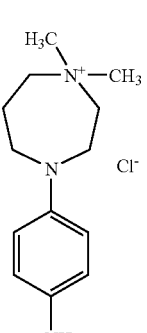 | 4-(4-aminophenyl)-1,1-dimethyl[1,4]diazepam-1-ium chloride |
| 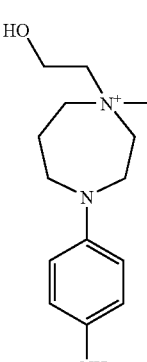 | 4-(4-aminophenyl)-1,1-bis-(2-hydroxyethyl)-[1,4]diazepam-1-ium chloride |

-continued

| Formula | Nomenclature |
|---|---|
| 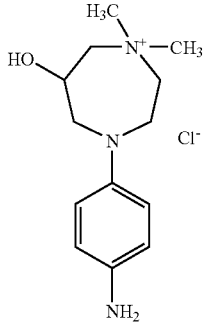 | 4-(4-aminophenyl)-6-hydroxy-1,1-dimethyl[1,4]-diazepan-1-ium chloride |
| 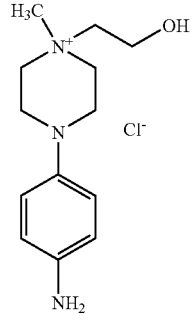 | 4-(4-aminophenyl)-1-(2-methoxyethyl)-1-methyl-piperazin-1-ium chloride |
| 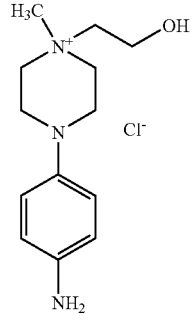 | 4-(4-aminophenyl)-1-(2-hydroxyethyl)-1-methyl[1,4]-diazepan-1-ium chloride |
| 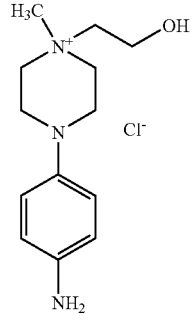 | 4-(4-aminophenyl)-1,2-dimethyl-1-m-tolylpiperazin-1-ium chloride |

-continued

| Formula | Nomenclature |
|---|---|
| 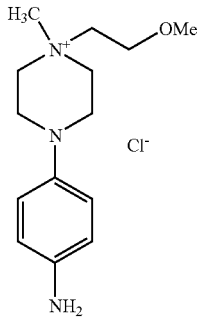 | 4-(4-aminophenyl)-1-(2-hydroxyethyl)-1-methyl-piperazin-1-ium chloride |
| 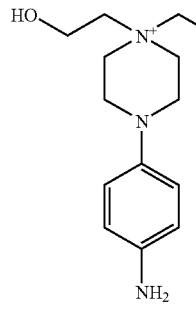 | 4-(4-aminophenyl)-1,1-bis-(2-hydroxyethyl)piperazin-1-ium chloride |
| 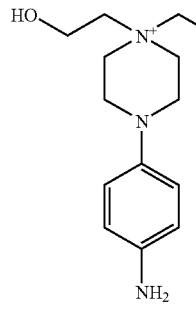 | 4-(4-aminophenyl)-1,2-dimethyl-1-m-tolylpiperazin-1-ium chloride |
| 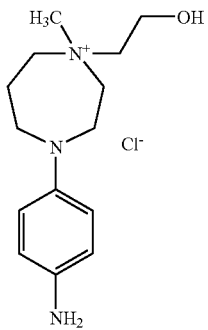 | 4-(4-aminophenyl)-1-ethyl-1-(2-hydroxyethyl)-piperazin-1-ium chloride |

-continued

| Formula | Nomenclature |
|---|---|
| 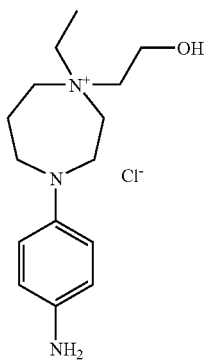 | 4-(4-aminophenyl)-1-(2-hydroxyethyl)-1-ethyl[1,4]-diazepan-1-ium chloride |
| 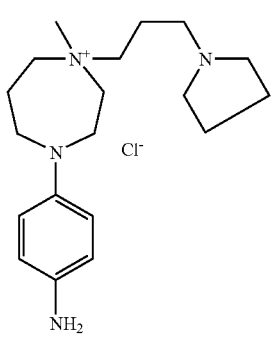 | 4-(4-aminophenyl)-1-methyl-1-(3-pyrrolidin-1-ylpropyl)[1,4]diazepam-1-ium chloride |
| 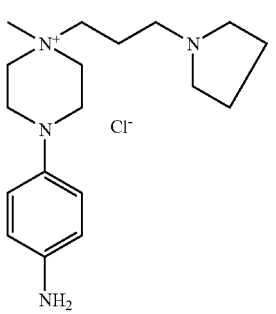 | 4-(4-aminophenyl)-1-methyl-1-(3-pyrrolidin-1-ylpropyl)piperazin-1-ium chloride |
| 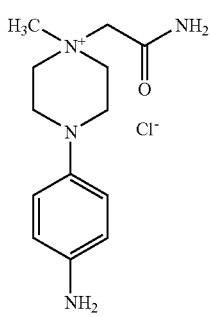 | 4-(4-aminophenyl)-1-carbamoylmethyl-1-methylpiperazin-1-ium chloride |

-continued

| Formula | Nomenclature |
|---|---|
| 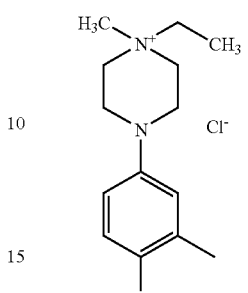 | 4-(4-amino-3-methylphenyl)-1-ethyl-1-methylpiperazin-1-ium chloride |
| 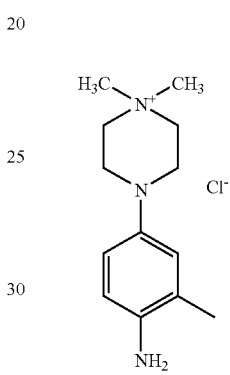 | 4-(4-amino-3-methyl-phenyl)-1,1-dimethyl-piperazin-1-ium chloride |
| 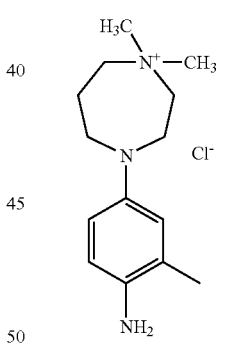 | 4-(4-amino-3-methylphenyl)-1,1-dimethyl[1,4]diazepam-1-ium chloride |
| 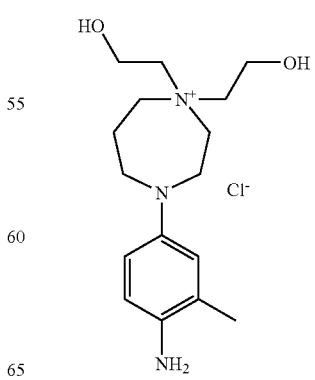 | 4-(4-amino-3-methyl-phenyl)-1,1-bis-(2-hydroxyethyl)[1,4]-diazepam-1-ium chloride |

-continued

| Formula | Nomenclature |
|---|---|
| 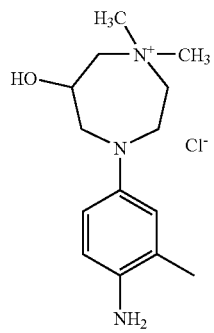 | 4-(4-amino-3-methylphenyl)-6-hydroxy-1,1-dimethyl[1,4]diazepam-1-ium chloride |
| 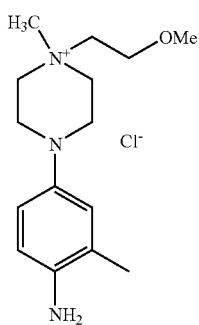 | 4-(4-amino-3-methyl-phenyl)-1-(2-methoxyethyl)-1-methylpiperazin-1-ium chloride |
| 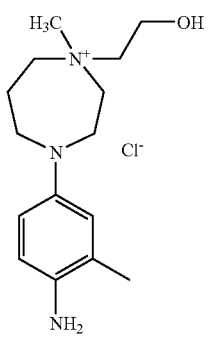 | 4-(4-amino-3-methylphenyl)-1-(2-hydroxyethyl)-1-methyl-[1,4]diazepam-1-ium chloride |
| 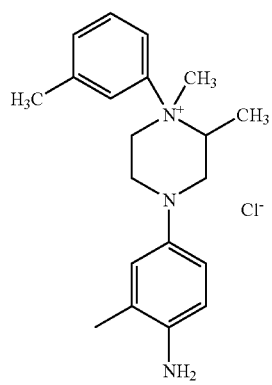 | 4-(4-amino-3-methyl-phenyl)-1,2-dimethyl-1-m-tolylpiperazin-1-ium chloride |

-continued

| Formula | Nomenclature |
|---|---|
| 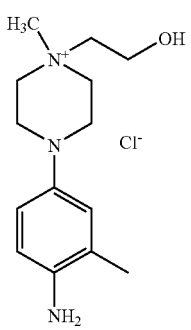 | 4-(4-amino-3-methylphenyl)-1-(2-hydroxyethyl)-1-methylpiperazin-1-ium chloride |
| 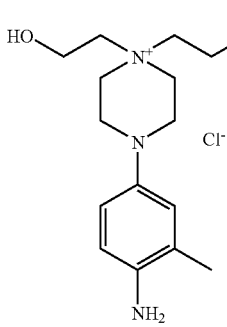 | 4-(4-amino-3-methyl-phenyl)-1,1-bis-(2-hydroxyethyl)piperazin-1-ium chloride |
| 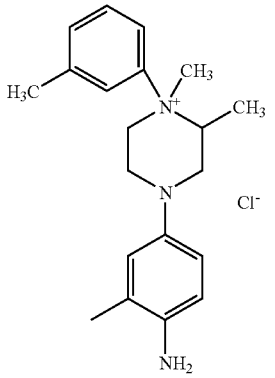 | 4-(4-amino-3-methylphenyl)-1,2-dimethyl-1-m-tolylpiperazin-1-ium chloride |
| 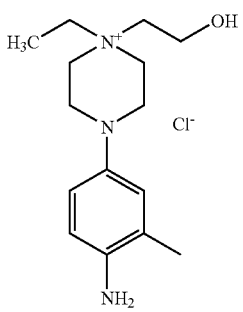 | 4-(4-amino-3-methyl-phenyl)-1-ethyl-1-(2-hydroxyethyl)piperazin-1-ium chloride |

-continued

| Formula | Nomenclature |
|---|---|
| | 4-(4-amino-3-methylphenyl)-1-(2-hydroxyethyl)1-ethyl[1,4]diazepam-1-ium chloride |
| | 4-(4-amino-3-methylphenyl)-1-methyl-1-(3-pyrrolidin-1-ylpropyl)-[1,4]diazepam-1-ium chloride |
| | 4-(4-amino-3-methylphenyl)-1-methyl-1-(3-pyrrolidin-1-ylpropyl)piperazin-1-ium chloride |
| | 4-(4-amino-3-aminophenyl)-1-carbamoyl-methyl-1-methylpiperazin 1-ium chloride |

Among these compounds, the derivatives of formula (I) may be, for example, 4-(4-aminophenyl)-1,1-dimethyl[1,4]diazepam-1-ium chloride, 4-(4-aminophenyl)-1,1-dimethylpiperazin-1-ium chloride and 4-(4-aminophenyl)-1-(2-hydroxyethyl)-1-methylpiperazin-1-ium chloride.

The carbon substituted with $R_3$ or with $R_4$ may be chosen from (R) and (S) configurations.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The at least one oxidation base of the disclosure is generally present in an amount ranging from 0.001% to 10% such as from 0.005% to 6% by weight relative to the total weight of the dye composition.

The dye composition disclosed herein may further comprise at least one coupler conventionally used for dyeing keratin fibres. Among these couplers that may be mentioned, for example, are meta-phenylenediamines, meta-aminophenols, meta-diphenols, naphthalene-based couplers, and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureido-aniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the addition salts thereof with an acid.

In the composition disclosed herein, the at least one coupler is generally present in an amount ranging from 0.001% to 10% such as from 0.005% and 6% by weight relative to the total weight of the dye composition.

The composition of the present disclosure may further comprise at least one additional oxidation base conventionally used in oxidation dyeing, other than those described above. By way of example, the at least one additional oxidation base may be chosen from para-phenylenediamines other than those described above, bis(phenyl)alkylenediamines, para-aminophenols, bis-para-aminophenols, ortho-aminophenols, ortho-phenylenediamines and heterocyclic bases, and the addition salts thereof.

Among the para-phenylenediamines which can be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof may, for example, be chosen.

Among the bis(phenyl)alkylenediamines which can be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4-amino-3'-methylphenyl)ethylenediamine and 1,8-bis(2,5-diaminophenoxy)-3,6-dioxaoctane, and the acid addition salts thereof.

Among the para-aminophenols which can be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols that can be mentioned, for example, are 2-aminophenol, 2-amino-5-methylphenol, 2-amino-6-methylphenol and 5-acetamido-2-aminophenol, and the acid addition salts thereof.

Among the heterocyclic bases, mention may be made, for example, of pyridine derivatives, pyrimidine derivatives and pyrazole derivatives.

Among the pyridine derivatives which may be mentioned are the compounds described, for example, in patent applications GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Other pyridine oxidation bases that may be useful in the present disclosure are the 3-aminopyrazolo[1,5-a]pyridine oxidation bases or the addition salts thereof described, for example, in patent application FR 2 801 308. By way of non-limiting example, mention may be made of pyrazolo[1,5-a]pyrid-3-ylamine; 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)-methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo-[1,5-a]pyrid-5-ol, 3-aminopyrazolo[1,5-a]pyrid-4-ol, 3-aminopyrazolo[1,5-a]pyrid-6-ol, 3-aminopyrazolo[1,5-a]pyrid-7-ol and the addition salts thereof.

Among the pyrimidine derivatives which may be mentioned are the compounds described, for example, in patent applications DE 2 359 399; JP 88-169 571; JP 05-63 124; EP 0 770 375; and WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine. Further non-limiting examples of the pyrimidine derivatives disclosed herein include pyrazolopyrimidine derivatives such as those mentioned in patent application FR-A-2 750 048, among which non-limiting mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]-pyrimidine-3,7-diamine and 3-amino-5-methyl-7-imidazolylpropylamino-pyrazolo[1,5-a]pyrimidine, and the acid addition salts thereof and the tautomeric forms thereof, when a tautomeric equilibrium exists.

Among the pyrazole derivatives which may be mentioned are the compounds described in patent applications DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The oxidation base present in the composition of the invention is generally present in an amount ranging from 0.001% to 10% by weight relative to the total weight of the dye composition, for example, from 0.005% to 6%.

In general, the addition salts of the oxidation bases and of the couplers that may be used in the context of the disclosure may be chosen, for example, from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, ammonia, amines and alkanolamines.

The dye composition in accordance with the invention may also comprise at least one direct dye that may be chosen from, for example, nitrobenzene dyes, azo direct dyes and methinic direct dyes. These direct dyes may be of nonionic, anionic or cationic nature.

The medium that is suitable for dyeing, also known as the dye support, generally comprises, for example, water or a mixture of water and at least one organic solvent to dissolve the compounds that would not be sufficiently water-soluble. Examples of organic solvents that may be mentioned include $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether; and aromatic alcohols such as benzyl alcohol and phenoxyethanol, and mixtures thereof.

The solvents may be present in proportions ranging from, for example, 1% to 40% by weight relative to the total weight of the dye composition, such as from 5% to 30% by weight.

The dye composition in accordance with the invention may also comprise various adjuvants conventionally used in compositions for dyeing the hair, such as anionic, cationic, nonionic, amphoteric and zwitterionic surfactants and mixtures thereof; anionic, cationic, nonionic, amphoteric and zwitterionic polymers and mixtures thereof; inorganic and organic thickeners, such as anionic, cationic, nonionic and amphoteric associative polymeric thickeners; antioxidants; penetration agents; sequestering agents; fragrances; buffers; dispersing agents; packaging agents such as, for example, silicones, which may or may not be volatile or modified; film-forming agents; ceramides; preserving agents; and opacifiers.

The above adjuvants are each generally present in an amount ranging from 0.01% to 20% by weight relative to the weight of the composition.

Needless to say, a person skilled in the art will take care to select this or these optional additional compounds such that the advantageous properties intrinsically associated with the oxidation dye composition disclosed herein are not, or are not substantially, adversely affected by the addition(s) envisaged.

The pH of the dye composition in accordance with the invention generally ranges from about 3 to 12 such as from 5 to 11. It may be adjusted to the desired value using acidifying or basifying agents usually used in the dyeing of keratin fibres, or alternatively using standard buffer systems.

Among the acidifying agents that may be mentioned, for example, are inorganic and organic acids such as hydrochloric acids; orthophosphoric acids; sulphuric acids; carboxylic acids such as acetic acid, tartaric acid, citric acid and lactic acid; and sulphonic acids.

Among the basifying agents that may be mentioned, for example, are aqueous ammonia; alkaline carbonates; alkanolamines such as mono-, di- and triethanolamine and derivatives thereof; sodium hydroxide; potassium hydroxide; and the compounds of formula (III) below:

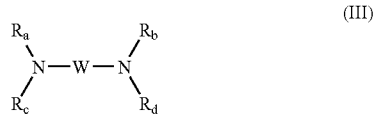

(III)

wherein

W is a propylene residue that is unsubstituted or substituted with a group chosen from hydroxyl groups and $C_1$–$C_4$ alkyl radicals;

$R_a$, $R_b$, $R_c$ and $R_d$, which may be identical or different, are chosen from a hydrogen atom, $C_1$–$C_4$ alkyl radicals and $C_1$–$C_4$ hydroxyalkyl radicals.

The dye composition disclosed herein may be in various forms, such as in the form of liquids, creams or gels, or in any other form that is suitable for dyeing keratin fibres, for example, human hair.

One process of the present disclosure is a process in which the composition disclosed herein as described above is applied to the fibres, and the colour is developed using an oxidizing agent. The colour may be developed at acidic, neutral or alkaline pH and the oxidizing agent may be added to the composition disclosed herein just at the time of use, or it may be used within an oxidizing composition, which is applied simultaneously or sequentially to the composition of the disclosure.

According to one non-limiting embodiment, the composition disclosed herein is mixed, for example, at the time of use, with a composition comprising, in a medium that is suitable for dyeing, at least one oxidizing agent, this oxidizing agent being present in an amount that is sufficient to develop a coloration. The mixture obtained is then applied to the keratin fibres. After an action time of 3 to 50 minutes, such as 5 to 30 minutes, the keratin fibres are rinsed, washed with shampoo, rinsed again and then dried.

The oxidizing agents conventionally used for the oxidation dyeing of keratin fibres may be, for example, hydrogen peroxide; urea peroxide; alkali metal bromates; persalts such as perborates and persulphates; peracids; and oxidase enzymes, among which mention may be made, for example, of peroxidases; 2-electron oxidoreductases such as uricases; and 4-electron oxygenases, for instance laccases. Hydrogen peroxide may, for example, be an oxidizing agent of the present disclosure.

The oxidizing composition may also comprise various adjuvants conventionally used in compositions for dyeing the hair and as defined above.

The pH of the oxidizing composition comprising the oxidizing agent is such that, after mixing with the dye composition, the pH of the resulting composition applied to the keratin fibres may range, for example, from 3 to 12 approximately such as from 5 to 11. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels or in any other form that is suitable for dyeing keratin fibres, such as human hair.

Another subject of the disclosure is a multi-compartment dyeing device or "kit", comprising a first compartment comprising the dye composition disclosed herein and a second compartment comprising an oxidizing composition. This device may be equipped with a means for applying the desired mixture to the hair, such as the devices described in patent FR-2 586 913 in the name of the Applicant.

Using this device, it is possible to dye keratin fibres by means of a process comprising mixing a dye composition comprising at least one oxidation base of formula (I) with an oxidizing agent, and applying the mixture obtained to the keratin fibres for a time that is sufficient to develop the desired coloration.

One embodiment of the disclosure is the para-phenylenediamine derivative of formula (I), wherein z is equal to 0, n is equal to 0, m is equal to 0, and $R_2$ and $R'_2$ are methyl radicals, and the addition salts thereof.

The para-phenylenediamine derivatives of formula (I) are obtained by reducing the para-nitroaniline derivatives of formula (II) below and their addition salts:

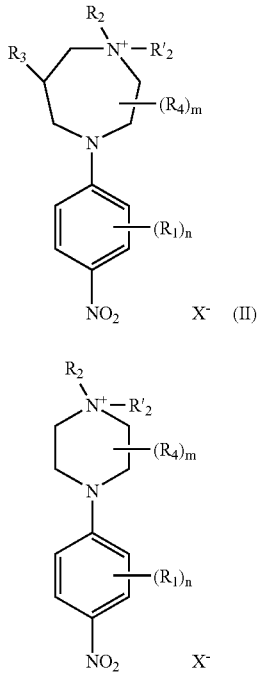

wherein the radicals $R_1$, $R_2$, $R'_2$, $R_3$ and $R_4$ and the integers n and m are as defined above. As used herein, formula (II) refers to both (IIa) and (IIb) and their acid addition salts.

A subject of the disclosure is also the para-nitroaniline derivatives of formula (II), with the exception of 4-(4-nitrophenyl)-1,1-dimethylpiperazin-1-ium.

The examples that follow serve to illustrate the invention without, however, being limiting in nature.

EXAMPLES

Example 1

Synthesis of 4-(4-aminophenyl)-1,1-dimethyl[1,4]diazepam-1-ium chloride dihydrochloride (4)

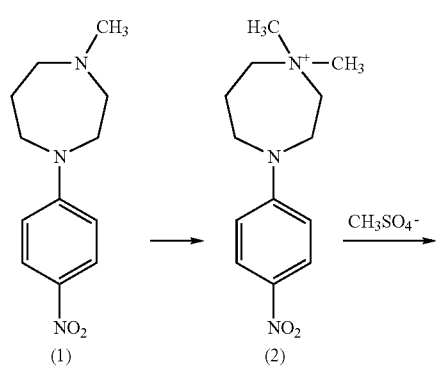

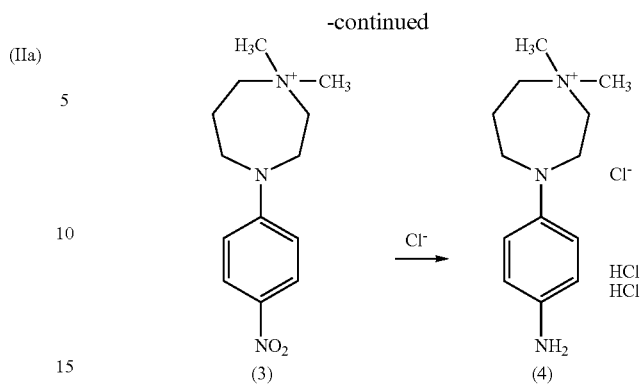

Synthesis of 1,1-dimethyl-4-(4-nitrophenyl)[1,4]diazepam-1-ium methyl sulphate (2)

23.5 g (0.1 mol) of 1-methyl-4-(4-nitrophenyl)[1,4]diazepane (1) were dissolved in 400 ml of ethyl acetate at room temperature, in a reactor.

11.4 ml (0.12 mol) of methyl sulphate were added dropwise, followed by stirring at room temperature for 4 hours. The reaction was exothermic (28° C.) and a crystalline yellow precipitate formed.

The solid was filtered off under vacuum and then recrystallized from ethyl acetate. The crystals obtained were dried under vacuum at 40° C. over phosphorus pentoxide. 35.6 g of yellow crystals were obtained (yield=98%).

The elemental analysis for $C_{14}H_{23}N_3SO_4$ was as follows:

|  | C % | H % | N % | O % | S % |
|---|---|---|---|---|---|
| Calculated: | 46.53 | 6.41 | 11.63 | 26.56 | 8.87 |
| Found: | 46.23 | 6.42 | 11.64 | 26.77 | 8.88 |

Synthesis of 1,1-dimethyl-4-(4-nitrophenyl)[1,4]diazepam-1-ium chloride (3)

The anion exchange was performed by passing a solution of 35.2 g (0.0974 mol) of 1,1-dimethyl-4-(4-nitrophenyl)[1,4]diazepam-1-ium methyl sulphate (2), obtained above in the preceding step, in a water/ethanol mixture through 190 g of Amberlite IRA402 resin.

After evaporation to dryness under reduced pressure and recrystallization from 120 ml of 96° ethanol, 26.4 g (yield=95%) of a crystalline yellow compound was obtained.

The results obtained by $^1$H NMR were as follows:
$^1$H (400 MHz, DMSO, D6): 2.31 (m, 2H), 3.25 (s, 6H), 3.6 (m, 2H), 3.65 (m, 2H), 3.72 (m, 2H), 3.97 (m 2H), 6.93 (m, 2H), 8.07 (m, 2H)

Synthesis of 4-(4-aminophenyl)-1,1-dimethyl[1,4]diazepam-1-ium chloride dihydrochloride (4)

22.9 g (0.08 mol) of 1,1-dimethyl-4-(4-nitrophenyl)[1,4] diazepam-1-ium chloride (3), obtained above in the preceding step, 6 g of palladium-on-charcoal (comprising 50% water), 400 ml of 96° ethanol and 150 ml of water were placed in a one-liter hydrogenator.

The reduction was performed over one hour at a hydrogen pressure of about 5 bar and at a temperature of 55° C.

After filtering off the catalyst under nitrogen, the reaction medium was poured onto aqueous hydrochloric acid. The filtrate was evaporated to dryness under reduced pressure. After recrystallization from a mixture of ethanol, hydrochloric acid and water, and drying at 45° C. under vacuum and over potassium hydroxide, 17.8 g of white crystals (yield=67%) were obtained.

The elemental analysis for $C_{13}H_{24}N_3Cl_3 \cdot H_2O$ is as follows:

|  | C % | H % | N % | O % | Cl % |
|---|---|---|---|---|---|
| Calculated: | 45.03 | 7.56 | 12.12 | 4.61 | 30.68 |
| Found: | 45.19 | 7.58 | 12.14 | 4.67 | 30.19 |

The results obtained by $^1$H NMR were as follows:

$^1$H (400 MHz, $D_2O$): 2.23 (m, 2H), 3.11 (s, 6H), 3.5 (m, 2H), 3.54 (m, 2H), 3.64 (m, 2H), 3.78 (m, 2H), 6.99 (m, 2H), 7.3 (m, 2H).

Example 2

Synthesis of 4-(4-aminophenyl)-1,1-dimethylpiperazin-1-ium chloride dihydrochloride (4)

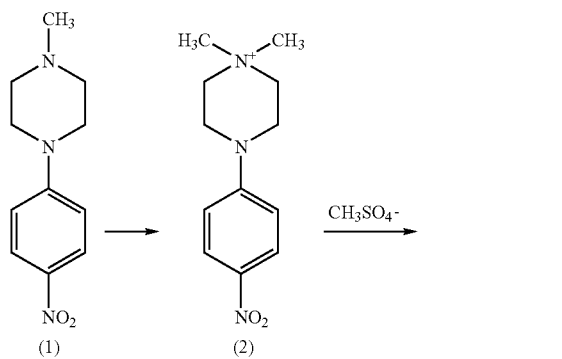

Synthesis of 1,1-dimethyl-4-(4-nitrophenyl)piperazin-1-ium methyl sulphate (2)

22.1 g (0.1 mol) of 1-methyl-4-(4-nitrophenyl)piperazine (1) were dissolved in 400 ml of ethyl acetate at room temperature, in a reactor.

11.4 ml (0.12 mol) of methyl sulphate were added dropwise while stirring, and the stirring is continued at room temperature for 4 hours. The yellow precipitate formed is filtered off under vacuum, recrystallized from ethyl acetate and dried under vacuum at 35° C. over phosphorus pentoxide. 34.3 g of yellow crystals were obtained (yield=99%).

Synthesis of 1,1-dimethyl-4-(4-nitrophenyl)piperazin-1-ium chloride (3)

The anion exchange was performed by passing a solution of 33.0 g (0.095 mol) of 1,1-dimethyl-4-(4-nitrophenyl)piperazin-1-ium methyl sulphate (2), obtained above the in the preceding step, in a water/ethanol mixture through 120 g of Amberlite IRA402 resin.

After evaporation to dryness under reduced pressure, 20.0 g of a yellow crystalline compound were obtained (yield=77%).

The results obtained by $^1$H NMR were as follows:

$^1$H NMR (400 MHz, DMSO, D6): 3.235 (s, 6H, N—$(CH_3)_2$); 3.37 (s, 3H, $CH_3OSO_3$—); 3.58 (m, 4H, $CH_2$); 3.829 (m, 4H, $CH_2$); 7.15 (d, 2H, ortho to N); 8.14 (d, 2H, ortho to $NO_2$).

Synthesis of 4-(4-aminophenyl)-1,1-dimethylpiperazin-1-ium chloride dihydrochloride (4)

19.0 g (0.07 mol) of 1,1-dimethyl-4-(4-nitrophenyl)piperazin-1-ium chloride (3), obtained above in the preceding step, 5 g of palladium-on-charcoal (containing 50% water), 400 ml of 96° ethanol and 150 ml of water were placed in a one-liter hydrogenator.

The reduction was performed over one and a half hours under a hydrogen pressure of about 6 bar and at a temperature of 50° C.

After filtering off the catalyst under nitrogen, the reaction medium was poured into aqueous hydrochloric acid. The filtrate was evaporated to dryness under reduced pressure. After drying at 45° C. under vacuum and over potassium hydroxide, 20.2 g of white crystals were obtained (yield=67%).

The elemental analysis for $C_{12}H_{22}N_3Cl_3 \cdot 1.5H_2O$ was as follows:

|  | C % | H % | N % | O % | Cl % |
|---|---|---|---|---|---|
| Calculated: | 42.18 | 7.37 | 12.30 | 7.02 | 31.13 |
| Found: | 42.46 | 7.14 | 12.43 | 7.86 | 30.09 |

The results obtained by $^1$H NMR were as follows:

$^1$H NMR (400 MHz, $D_2O$): 3.33 (s, 6H, $CH_3$); 3.71 (m, 8H, $CH_2$); 7.32 (m, 2H, ortho to N); 7.49 (m, 2H, ortho to $NH_2$).

Example 3

Synthesis of 4-(4-aminophenyl)-1-(2-hydroxyethyl)-1-methylpiperazin-1-ium chloride dihydrochloride (4)

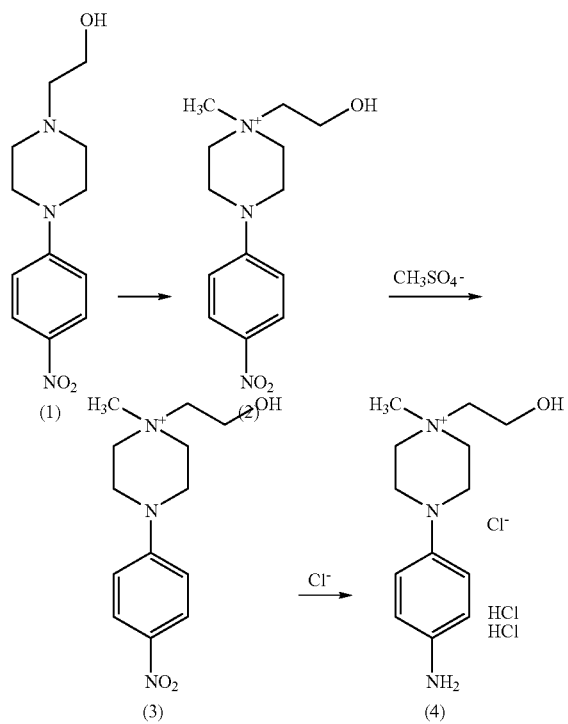

Synthesis of 1-(2-hydroxyethyl)-1-methyl-4-(4-nitrophenyl)piperazin-1-ium methyl sulphate (2)

25.1 g (0.1 mol) of 2-[4-(4-nitrophenyl)piperazin-1-yl]ethanol (1) were dissolved in 500 ml of ethyl acetate heated to 40° C., in a reactor.

11.4 ml (0.12 mol) of methyl sulphate were added dropwise while stirring, and the stirring is continued at room temperature for 5 hours. The yellow precipitate formed is filtered off under vacuum, recrystallized from ethyl acetate and dried under vacuum at 40° C. over phosphorus pentoxide. 38.0 g (quantitative yield) of yellow crystals were obtained.

The elemental analysis for $C_{14}H_{23}N_3SO_7$ is as follows:

|  | C % | H % | N % | O % | S % |
|---|---|---|---|---|---|
| Calculated: | 44.55 | 6.14 | 11.13 | 29.67 | 8.50 |
| Found: | 44.63 | 6.14 | 11.20 | 29.55 | 8.56 |

The anion exchange was performed by passing a solution of 38.0 g (0.1 mol) of 1-(2-hydroxyethyl)-1-methyl-4-(4-nitrophenyl)piperazin-1-ium methyl sulphate (2), obtained above in the preceding step, in a water/ethanol mixture through 190 g of Amberlite IRA402 resin.

After evaporation to dryness under reduced pressure and recrystallization from 220 ml of refluxing 96° ethanol, 27.0 g of a yellow crystalline compound were obtained (yield=71%).

The results obtained by $^1$H NMR were as follows:

$^1$H NMR (400 MHz, DMSO, D6): 3.25 (s, 3H, CH$_3$N); 3.373 (s, 3H, CH$_3$OSO$_3$—); 3.615–3.925 (m, 12H, CH$_2$); 5.52 (t, 1H, OH); 7.148 (d, 2H, ortho to N); 8.146 (d, 2H, ortho to NO$_2$).

Synthesis of 4-(4-aminophenyl)-1-(2-hydroxyethyl)-1-methylpiperazin-1-ium chloride dihydrochloride (4)

14.1 g (0.08 mol) of 1-(2-hydroxyethyl)-1-methyl-4-(4-nitrophenyl)piperazin-1-ium chloride (3), obtained above in the preceding step, 6 g of palladium-on-charcoal (comprising 50% water), 400 ml of 96° ethanol and 150 ml of water are placed in a one-liter hydrogenator.

The reduction is performed over 2 hours under a hydrogen pressure of about 5 bar and at a temperature of 50° C.

After filtering off the catalyst under nitrogen, the reaction medium was poured into aqueous hydrochloric acid. The filtrate was evaporated to dryness under reduced pressure. After drying at 45° C. under vacuum and over potassium hydroxide, 23.2 g of white crystals were obtained (yield=80%).

The results obtained by $^1$H NMR were as follows:

$^1$H NMR (400 MHz, DMSO, D6): 3.24 (s, 3H, CH$_3$); 3.53 (m, 10H, CH$_2$); 3.87 (m, 2H, CH$_2$); 7.08 (d, 2H, ortho to N); 7.31 (d, 2H, ortho to NH$_2$); 9.25 (m, 1H, OH); 10.52 (m, 2H, NH$_2$).

Examples of Dyeing

Examples 1 to 5

Dyeing in Acidic Medium Using 4-(4-aminophenyl)-1,1-dimethyl[1,4]diazepam-1-ium chloride dihydrochloride The dye compositions below were prepared:

|  | Example | | | | |
|---|---|---|---|---|---|
|  | 1 | 2 | 3 | 4 | 5 |
| 4-(4-Aminophenyl)-1,1-dimethyl[1,4]-diazepan-1-ium chloride dihydrochloride (base) | $10^{-3}$ mol | $10^{-3}$ mol | $10^{-3}$ mol | $10^{-3}$ mol | $10^{-3}$ mol |
| 2-(2,4-Diaminophenoxy) ethanol dihydrochloride (coupler) | $10^{-3}$ mol | — | — | — | — |
| 3-Amino-2-chloro-6- | — | $10^{-3}$ mol | — | — | — |

-continued

| | | | | | |
|---|---|---|---|---|---|
| methylphenol hydrochloride (coupler) | | | | | |
| 2-Methyl-5-aminophenol (coupler) | — | — | $10^{-3}$ mol | — | — |
| 2-Aminopyridin-3-ol (coupler) | — | — | — | $10^{-3}$ mol | — |
| 1H-Indol-6-ol (coupler) | — | — | — | — | $10^{-3}$ mol |
| Dye support (2) | (*) | (*) | (*) | (*) | (*) |
| Demineralized water qs | 100 g | 100 g | 100 g | 100 g | 100 g |

(*) Dye support (2) pH 7

| | |
|---|---|
| 96° ethyl alcohol | 20.8 g |
| Sodium metabisulphite as an aqueous 35% solution | 0.23 g A.M. |
| Pentasodium salt of diethylenetri-aminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After leaving to act for 30 minutes, the locks were rinsed, washed with a standard shampoo, rinsed again and then dried.

The following dyeing results were obtained.

| | Example | | | | |
|---|---|---|---|---|---|
| | 1 | 2 | 3 | 4 | 5 |
| Shade observed | Violet-blue | Violet | Violet-beige | Violet-beige | Beige |

Examples 6 to 8

Dyeing in Alkaline Medium Using 4-(4-aminophenyl)-1,1-dimethyl[1,4]diazepam-1-ium chloride dihydrochloride The dye compositions below were prepared:

| | Example | | |
|---|---|---|---|
| | 6 | 7 | 8 |
| 4-(4-Aminophenyl)-1,1-dimethyl[1,4]-diazepam-1-ium chloride dihydro-chloride (base) | $10^{-3}$ mol | $10^{-3}$ mol | $10^{-3}$ mol |
| 2-(2,4-Diaminophenoxy)ethanol dihydrochloride (coupler) | $10^{-3}$ mol | — | — |
| 4,6-Dimethyl-2H-pyrazolo[3,2c][1,2,4]triazole (coupler) | — | $10^{-3}$ mol | — |
| 3-Amino-2-chloro-6-methylphenol hydrochloride (coupler) | — | — | $10^{-3}$ mol |
| Dye support (1) | (*) | (*) | (*) |
| Demineralized water qs | 100 g | 100 g | 100 g |

(*) Dye support (1) pH 9.5

| | |
|---|---|
| 96° ethyl alcohol | 20.8 g |
| Sodium metabisulphite as an aqueous 35% solution | 0.23 g A.M. |
| Pentasodium salt of diethylenetri-aminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After leaving to act for 30 minutes, the locks were rinsed, washed with a standard shampoo, rinsed again and then dried.

The following dyeing results were obtained.

| | Example | | |
|---|---|---|---|
| | 6 | 7 | 8 |
| Shade observed | Violet-blue | Red-violet | Violet |

Examples 9 to 11

Dyeing in Acidic Medium Using 4-(4-aminophenyl)-1,1-dimethylpiperazin-1-ium chloride dihydrochloride The dye compositions below were prepared:

|  | Example | | |
| --- | --- | --- | --- |
|  | 9 | 10 | 11 |
| 4-(4-Aminophenyl)-1,1-dimethyl-piperazin-1-ium chloride dihydrochloride (base) | $10^{-3}$ mol | $10^{-3}$ mol | $10^{-3}$ mol |
| 2-(2,4-Diaminophenoxy)ethanol dihydrochloride (coupler) | $10^{-3}$ mol | — | — |
| 2-Aminopyridin-3-ol (coupler) | — | $10^{-3}$ mol | — |
| 1H-Indol-6-ol (coupler) | — | — | $10^{-3}$ mol |
| Dye support (2) | (*) | (*) | (*) |
| Demineralized water qs | 100 g | 100 g | 100 g |

| (*) Dye support (2) pH 7 | |
| --- | --- |
| 96° ethyl alcohol | 20.8 g |
| Sodium metabisulphite as an aqueous 35% solution | 0.23 g A.M. |
| Pentasodium salt of diethylenetri-aminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After leaving to act for 30 minutes, the locks were rinsed, washed with a standard shampoo, rinsed again and then dried.

The following dyeing results were obtained.

|  | Example | | |
| --- | --- | --- | --- |
|  | 9 | 10 | 11 |
| Shade observed | Beige | Orange | Orange-grey |

Example 12

Dyeing in Alkaline Medium Using 4-(4-aminophenyl)-1,1-dimethylpiperazin-1-ium chloride dihydrochloride The dye composition below was prepared:

|  | Example 12 |
| --- | --- |
| 4-(4-Aminophenyl)-1,1-dimethylpiperazin-1-ium chloride dihydrochloride (base) | $10^{-3}$ mol |
| 2-(2,4-Diaminophenoxy)ethanol dihydrochloride (coupler) | $10^{-3}$ mol |
| Dye support (1) | (*) |
| Demineralized water qs | 100 g |

| (*) Dye support (1) pH 9.5 | |
| --- | --- |
| 96° ethyl alcohol | 20.8 g |
| Sodium metabisulphite as an aqueous 35% solution | 0.23 g A.M. |
| Pentasodium salt of diethylenetri-aminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, the composition was mixed with an equal weight of 20-volumes aqueous hydrogen peroxide solution (6% by weight). A final pH of 9.5 was obtained.

The mixture obtained was applied to locks of grey hair comprising 90% white hairs. After leaving to act for 30 minutes, the locks were rinsed, washed with a standard shampoo, rinsed again and then dried.

The following dyeing results were obtained.

|  | Example 12 |
| --- | --- |
| Shade observed | Beige |

Examples 13 to 15

Dyeing in Acidic Medium Using 4-(4-aminophenyl)-1-(2-hydroxyethyl)-1-methylpiperazin-1-ium chloride dihydrochloride The dye compositions below were prepared:

|  | Example | | |
| --- | --- | --- | --- |
|  | 13 | 14 | 15 |
| 4-(4-Aminophenyl)-1-(2-hydroxyethyl)-1-methylpiperazin-1-ium chloride dihydrochloride (base) | $10^{-3}$ mol | $10^{-3}$ mol | $10^{-3}$ mol |
| 2-(2,4-Diaminophenoxy)ethanol dihydrochloride (coupler) | $10^{-3}$ mol | — | — |
| 2-Aminopyridin-3-ol (coupler) | — | $10^{-3}$ mol | — |
| 1H-Indol-6-ol (coupler) | — | — | $10^{-3}$ mol |
| Dye support (2) | (*) | (*) | (*) |
| Demineralized water qs | 100 g | 100 g | 100 g |

| (*) Dye support (2) pH 7 | |
| --- | --- |
| 96° ethyl alcohol | 20.8 g |
| Sodium metabisulphite as an aqueous 35% solution | 0.23 g A.M. |
| Pentasodium salt of diethylenetri-aminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After leaving to act for 30 minutes, the locks were rinsed, washed with a standard shampoo, rinsed again and then dried.

The following dyeing results were obtained.

|  | Example | | |
| --- | --- | --- | --- |
|  | 13 | 14 | 15 |
| Shade observed | Beige | Orange | Orange-grey |

Example 16

Dyeing in Alkaline Medium Using 4-(4-aminophenyl)-1-(2-hydroxyethyl)-1-methylpiperazin-1-ium chloride dihydrochloride The dye composition below was prepared:

|  | Example 16 |
| --- | --- |
| 4-(4-Aminophenyl)-1-(2-hydroxyethyl)-1-methylpiperazin-1-ium chloride dihydrochloride (base) | $10^{-3}$ mol |
| 2-(2,4-Diaminophenoxy)ethanol dihydrochloride (coupler) | $10^{-3}$ mol |
| Dye support (1) | (*) |
| Demineralized water qs | 100 g |
| (*) Dye support (1) pH 9.5 | |
| 96° ethyl alcohol | 20.8 g |
| Sodium metabisulphite as an aqueous 35% solution | 0.23 g A.M. |
| Pentasodium salt of diethylenetri-aminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, the composition was mixed with an equal weight of 20-volumes aqueous hydrogen peroxide solution (6% by weight). A final pH of 9.5 was obtained.

The mixture obtained was applied to locks of grey hair comprising 90% white hairs. After leaving to act for 30 minutes, the locks were rinsed, washed with a standard shampoo, rinsed again and then dried.

The following dyeing results were obtained.

|  | Example 16 |
| --- | --- |
| Shade observed | Beige |

What is claimed is:

1. A composition for dyeing keratin fibres, comprising, in a cosmetic medium that is suitable for dyeing, at least one para-phenylenediamine derivative chosen from formula (Ia), formula (Ib), and their addition salts:

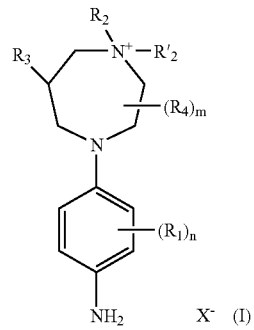

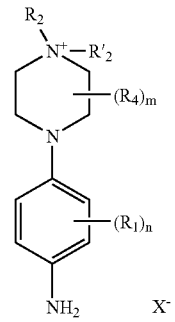

wherein:

$R_1$ is chosen from:

a halogen atom; and saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;

n ranges from 0 to 4, wherein, when n is greater than 1, each $R_1$ may be identical or different;

$R_2$ and $R'_2$, which may be identical or different, are chosen from:

saturated and unsaturated alkyl radicals, wherein saturated and unsaturated alkyl radicals may optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —$CH_2R$ radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;

aryl radicals; and benzyl radicals;

$R_3$ is chosen from:

a hydrogen atom;

optionally unsaturated alkyl radicals;

hydroxyl radicals;

hydroxyalkyl radicals;

alkoxy radicals;

alkoxyalkyl radicals;

alkylcarbonyl radicals;
hydroxyalkoxyalkyl radicals;
amino radicals, wherein the amine is optionally monosubstituted or disubstituted with a radical chosen from alkyl radicals, acetyl radicals and hydroxyalkyl radicals;
alkyl radicals substituted with at least one hydroxy radical and at least one amino radical;
monoalkylamino radicals;
dialkylamino radicals;
aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion.

2. The composition according to claim 1, wherein n is equal to 0 or $R_1$ is chosen from alkyl radicals, hydroxyalkyl radicals, aminoalkyl radicals, alkoxy radicals, and hydroxyalkoxy radicals.

3. The composition according to claim 2, wherein n is equal to 0 or $R_1$ is chosen from methyl radicals, hydroxymethyl radicals, 2-hydroxyethyl radicals, 1,2-dihydroxyethyl radicals, methoxy radicals, isopropyloxy radicals, and 2-hydroxyethoxy radicals.

4. The composition according to claim 1, wherein n is equal to 0 or 1.

5. The composition according to claim 1, wherein $R_2$ is chosen from alkyl radicals and alkyl radicals substituted with a saturated or unsaturated heterocyclic radical comprising 4, 5, 6 or 7 atoms, wherein at least one hetero atom of which is chosen from nitrogen; oxygen; sulphur; and —$CH_2R$ radicals, wherein R is an alkyl radical substituted with at least one hydroxyl radical.

6. The composition according to claim 5, wherein $R_2$ is chosen from a 2-hydroxyethyl radical, a 2,3-dihydroxypropyl radical, a 3-(1-pyrrolidinyl)propyl radical, and a methyl radical.

7. The composition according to claim 1, wherein $R'_2$ is chosen from saturated and unsaturated alkyl radicals and —$CH_2R$ radicals, wherein R is an alkyl radical substituted with at least one group chosen from hydroxyls, aminos, monoalkylaminos and dialkylaminos.

8. The composition according to claim 7, wherein $R'_2$ is chosen from a methyl radical, an ethyl radical, and a 2-hydroxyethyl radical.

9. The composition according to claim 1, wherein $R_3$ is chosen from a hydrogen atom, alkyl radicals, hydroxyalkyl radicals, aminoalkyl radicals, carboxyl radicals, carbamoyl radicals, hydroxyl radicals, alkoxy radicals, amino radicals, monoalkylamino radicals, and dialkylamino radicals.

10. The composition according to claim 9, wherein $R_3$ is chosen from a hydrogen atom, hydroxyl radicals, carboxyl radicals, carbamoyl radicals, amino radicals, hydroxymethyl radicals, and aminomethyl radicals.

11. The composition according to claim 1, wherein m is equal to 0 or $R_4$ is chosen from alkyl radicals, hydroxyalkyl radicals, aminoalkyl radicals, carboxyl radicals, carbamoyl radicals, monoalkylcarbamoyl radicals, and dialkylcarbamoyl radicals.

12. The composition according to claim 11, wherein m is equal to 0 or 1.

13. The composition according to claim 1, wherein the at least one para-phenylenediamine derivative is chosen from 4-(4-aminophenyl)-1-ethyl-1-methylpiperazin-1-ium chloride, 4-(4-aminophenyl)-1,1-dimethylpiperazin-1-ium chloride 4-(4-aminophenyl)-1,1-dimethyl[1,4]diazepan-1-ium chloride 4-(4-aminophenyl)-1,1-bis-(2-hydroxyethyl)-[1,4]diazepan-1-ium chloride 4-(4-aminophenyl)-6-hydroxy-1,1-dimethyl[1,4]diazepan-1-ium chloride 4-(4-aminophenyl)-1-(2-methoxyethyl)-1-methylpiperazin-1-ium chloride 4-(4-aminophenyl)-1-(2-hydroxyethyl)-1-methyl[1,4]diazepan-1-ium chloride 4-(4-aminophenyl)-1,2-dimethyl-1-m-tolylpiperazin-1-ium chloride 4-(4-aminophenyl)-1-(2-hydroxyethyl)-1-methylpiperazin-1-ium chloride 4-(4-aminophenyl)-1,1-bis-(2-hydroxyethyl)piperazin-1-ium chloride 4-(4-aminophenyl)-1,2-dimethyl-1-m-tolylpiperazin-1-ium chloride 4-(4-aminophenyl)-1-ethyl-1-(2-hydroxyethyl)piperazin-1-ium chloride 4-(4-aminophenyl)-1-(2-hydroxyethyl)-1-ethyl[1,4]diazepan-1-ium chloride 4-(4-aminophenyl)-1-methyl-1-(3-pyrrolidin-1-ylpropyl)[1,4]diazepan-1-ium chloride 4-(4-aminophenyl)-1-methyl-1-(3-pyrrolidin-1-ylpropyl)piperazin-1-ium chloride 4-(4-aminophenyl)-1-carbamoylmethyl-1-methylpiperazin-1-ium chloride 4-(4-amino-3-methylphenyl)-1-ethyl-1-methylpiperazin-1-ium chloride 4-(4-amino-3-methylphenyl)-1,1-dimethylpiperazin-1-ium chloride 4-(4-amino-3-methylphenyl)-1,1-dimethyl[1,4]diazepan-1-ium chloride 4-(4-amino-3-methylphenyl)-1,1-bis-(2-hydroxyethyl)[1,4]diazepan-1-ium chloride 4-(4-amino-3-methylphenyl)-6-hydroxy-1,1-dimethyl[1,4]diazepan-1-ium chloride 4-(4-amino-3-methylphenyl)-1-(2-methoxyethyl)-1-methylpiperazin-1-ium chloride 4-(4-amino-3-methylphenyl)-1-(2-hydroxyethyl)-1-methyl-[1,4]diazepan-1-ium chloride 4-(4-amino-3-methylphenyl)-1,2-dimethyl-1-m-tolylpiperazin-1-ium chloride, 4-(4-amino-3-methylphenyl)-1-(2-hydroxyethyl)-1-methylpiperazin-1-ium chloride, 4-(4-amino-3-methylphenyl)-1,1-bis-(2-hydroxyethyl)piperazin-1-ium chloride, 4-(4-amino-3-methylphenyl)-1,2-dimethyl-1-m-tolylpiperazin-1-ium chloride, 4-(4-amino-3-methylphenyl)-1-ethyl-1-(2-hydroxyethyl)piperazin-1-ium chloride, 4-(4-amino-3-methylphenyl)-1-(2-hydroxyethyl)-1-ethyl[1,4]diazepan-1-ium chloride, 4-(4-amino-3-methylphenyl)-1-methyl-1-(3-pyrrolidin-1-ylpropyl)[1,4]diazepan-1-ium chloride, 4-(4-amino-3-methylphenyl)-1-methyl-1-(3-pyrrolidin-1-ylpropyl)piperazin-1-ium chloride, and 4-(4-amino-3-aminophenyl)-1-carbamoylmethyl-1-methylpiperazin-1-ium chloride.

14. The composition according to claim 13, wherein the at least one para-phenylenediamine derivative is chosen from 4-(4-aminophenyl)-1,1-dimethyl[1,4]diazepan-1-ium chloride, 4-(4-aminophenyl)-1,1-dimethylpiperazin-1-ium chloride, and 4-(4-aminophenyl)-1-(2-hydroxyethyl)-1-methylpiperazin-1-ium chloride.

15. The composition according to claim 1, further comprising at least one coupler chosen from meta-phenylenediamines, meta-aminophenols, meta-diphenols, naphthalene-based couplers, and heterocyclic couplers, and the addition salts thereof.

16. The composition according to claim 15, wherein the amount of the at least one coupler ranges from 0.001% to 10% by weight relative to the total weight of the dye composition.

17. The composition of claim 16, wherein the amount of the at least one coupler ranges from 0.005% to 6% by weight relative to the total weight of the dye composition.

18. The composition according to claim 1, further comprising at least one additional oxidation base other than the the at least one para-phenylenediamine derivative, chosen from para-phenylenediamines, bis(phenyl)alkylenediamines, para-aminophenols, bis-para-aminophenols, ortho-aminophenols, ortho-phenylenediamines and heterocyclic bases, and the addition salts thereof.

19. The composition according to claim 18, wherein the amount of the at least one additional oxidation base ranges from 0.001% to 10% by weight relative to the total weight of the dye composition.

20. The composition according to claim 19, wherein the amount of the at least one additional oxidation base ranges from 0.005% to 6% by weight relative to the total weight of the dye composition.

21. A process for dyeing keratin fibres comprising applying a composition to keratin fibres in the presence of an oxidizing agent, for a time that is sufficient to develop a desired coloration, the composition comprising, in a cosmetic medium that is suitable for dyeing, at least one para-phenylenediamine derivative chosen from formula (Ia), formula (Ib), and their addition salts:

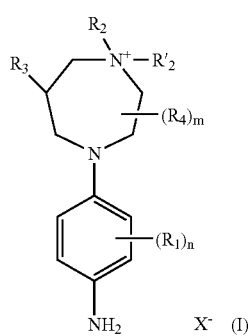

(Ia)

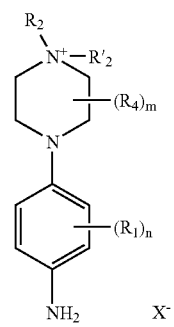

(Ib)

wherein:

R$_1$ is chosen from:

a halogen atom; and saturated and unsaturated C$_1$–C$_8$ aliphatic and alicyclic hydrocarbon-based chains, wherein at least one carbon atom is optionally replaced with at least one entity chosen from oxygen, nitrogen, silicon, sulphur, and SO$_2$ groups; and wherein R$_1$ does not comprise peroxide bonds or diazo, nitro or nitroso radicals;

n ranges from 0 to 4, wherein, when n is greater than 1, each R$_1$ may be identical or different;

R$_2$ and R'$_2$, which may be identical or different, are chosen from:

saturated and unsaturated alkyl radicals, wherein saturated and unsaturated alkyl radicals may be optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —CH$_2$R radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;

aryl radicals; and benzyl radicals;

R$_3$ is chosen from:

a hydrogen atom;

optionally unsaturated alkyl radicals;

hydroxyl radicals;

hydroxyalkyl radicals;

alkoxy radicals;

alkoxyalkyl radicals;

alkylcarbonyl radicals;

hydroxyalkoxyalkyl radicals;

amino radicals, wherein the amine is optionally monosubstituted or disubstituted with a radical chosen from alkyl radicals, acetyl radicals and hydroxyalkyl radicals;

alkyl radicals substituted with at least one hydroxy radical and at least one amino radical;

monoalkylamino radicals;

dialkylamino radicals;

aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion.

22. The process according to claim 21, wherein the oxidizing agent is chosen from hydrogen peroxide, urea peroxide, alkali metal bromates, persalts, peracids and oxidase enzymes.

23. A multi-compartment device comprising a first compartment comprising a composition for dyeing keratin fibres, and a second compartment comprising an oxidizing agent, the composition for dyeing keratin fibres comprising, in a cosmetic medium that is suitable for dyeing, at least one para-phenylenediamine derivative chosen from formula (Ia), formula (Ib), and their addition salts:

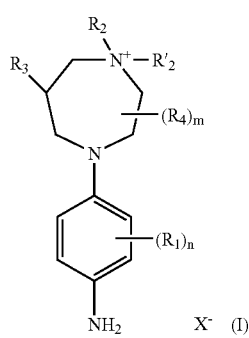

(Ia)

-continued

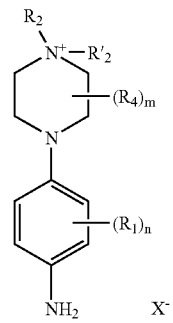

(Ib)

wherein:

$R_1$ is chosen from:

a halogen atom; and saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;

n ranges from 0 to 4, wherein, when n is greater than 1, each $R_1$ may be identical or different;

$R_2$ and $R'_2$, which may be identical or different, are chosen from:

saturated and unsaturated alkyl radicals, wherein saturated and unsaturated alkyl radicals may be optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —$CH_2R$ radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;

aryl radicals; and benzyl radicals;

$R_3$ is chosen from:

a hydrogen atom;

optionally unsaturated alkyl radicals;

hydroxyl radicals;

hydroxyalkyl radicals;

alkoxy radicals;

alkoxyalkyl radicals;

alkylcarbonyl radicals;

hydroxyalkoxyalkyl radicals;

amino radicals, wherein the amine is optionally monosubstituted or disubstituted with a radical chosen from alkyl radicals, acetyl radicals and hydroxyalkyl radicals;

alkyl radicals substituted with at least one hydroxy radical and at least one amino radical;

monoalkylamino radicals;

dialkylamino radicals;

aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion.

24. At least one para-Phenylenediamine derivative chosen from formula (Ia), formula (Ib), and their addition salts:

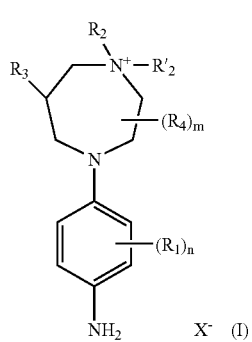

(Ia)

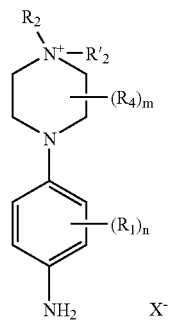

(Ib)

wherein:
$R_1$ is chosen from:
a halogen atom; and
saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;
n ranges from 0 to 4, wherein, when n is greater than 1, each $R_1$ may be identical or different;
$R_2$ and $R'_2$, which may be identical or different, are chosen from:
saturated and unsaturated alkyl radicals, wherein saturated and unsaturated alkyl radicals may be optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —$CH_2R$ radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;
aryl radicals; and
benzyl radicals;
$R_3$ is chosen from:
a hydrogen atom;
optionally unsaturated alkyl radicals;
hydroxyl radicals;
hydroxyalkyl radicals;
alkoxy radicals;
alkoxyalkyl radicals;
alkylcarbonyl radicals;
hydroxyalkoxyalkyl radicals;
amino radicals, wherein the amine is optionally monosubstituted or disubstituted with a radical chosen from alkyl radicals, acetyl radicals and hydroxyalkyl radicals;
alkyl radicals substituted with at least one hydroxy radical and at least one amino radical;
monoalkylamino radicals;
dialkylamino radicals;

aminoalkyl radicals, wherein the amine is optionally monosubstituted or disubstituted with a radical chosen from alkyl radicals, acetyl radicals and hydroxyalkyl radicals;

carboxyl radicals;

carboxyalkyl radicals;

carbamoyl radicals;

carbamoylalkyl radicals;

alkoxycarbonyl radicals;

monoalkylaminocarbonyl radicals;

dialkylaminocarbonyl radicals;

monoalkylaminocarbonylalkyl radicals; and dialkylaminocarbonylalkyl radicals;

$R_4$ is chosen from:

saturated and unsaturated alkyl radicals;

hydroxyalkyl radicals;

alkoxyalkyl radicals;

alkylcarbonyl radicals;

hydroxyalkoxyalkyl radicals;

aminoalkyl radicals, wherein the amine is optionally monosubstituted or disubstituted with a radical chosen from alkyl radicals, acetyl radicals and hydroxyalkyl radicals;

hydroxy radicals aminoalkyl radicals;

carboxyl radicals;

carboxyalkyl radicals;

carbamoyl radicals;

carbamoylalkyl radicals;

alkoxycarbonyl radicals;

monoalkylaminocarbonyl radicals;

dialkylaminocarbonyl radicals;

monoalkylaminocarbonylalkyl radicals; and dialkylaminocarbonylalkyl radicals;

m ranges from 0 to 4, wherein when m is greater than 1, each $R_4$ may be identical or different; and $X^-$ is a counterion;

wherein the at least one para-phenylenediamine derivative is not substituted with a diazacyclohexane ring wherein n is equal to 0, m is equal to 0 and $R_2$ and $R'_2$ are methyl radicals.

25. At least one para-Nitroaniline derivative chosen from formula (IIa), (IIb), and their addition salts:

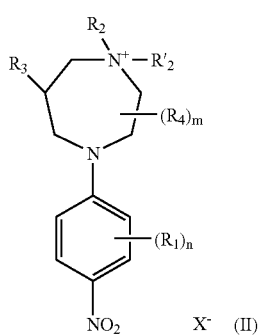

(IIa)

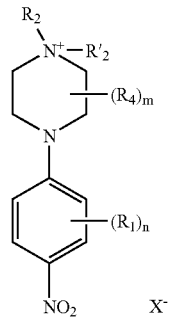

(IIb)

wherein:

$R_1$ is chosen from:

a halogen atom; and saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;

n ranges from 0 to 4, wherein, when n is greater than 1, each $R_1$ may be identical or different;

$R_2$ and $R'_2$, which may be identical or different, are chosen from:

saturated and unsaturated alkyl radicals, wherein saturated and unsaturated alkyl radicals may be optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —$CH_2R$ radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;

aryl radicals; and benzyl radicals;

$R_3$ is chosen from:

a hydrogen atom;

optionally unsaturated alkyl radicals;

hydroxyl radicals;

hydroxyalkyl radicals;

alkoxy radicals;

alkoxyalkyl radicals;

alkylcarbonyl radicals;

hydroxyalkoxyalkyl radicals;

amino radicals, wherein the amine is optionally monosubstituted or disubstituted with a radical chosen from alkyl radicals, acetyl radicals and hydroxyalkyl radicals;

alkyl radicals substituted with at least one hydroxy radical and at least one amino radical;

monoalkylamino radicals;

dialkylamino radicals;

aminoalkyl radicals, wherein the amine is optionally monosubstituted or disubstituted with a radical chosen from alkyl radicals, acetyl radicals and hydroxyalkyl radicals;

carboxyl radicals;

carboxyalkyl radicals;

carbamoyl radicals;

carbamoylalkyl radicals;

alkoxycarbonyl radicals;

monoalkylaminocarbonyl radicals;

dialkylaminocarbonyl radicals;

monoalkylaminocarbonylalkyl radicals; and dialkylaminocarbonylalkyl radicals;

R$_4$ is chosen from:

saturated and unsaturated alkyl radicals;

hydroxyalkyl radicals;

alkoxyalkyl radicals;

alkylcarbonyl radicals;

hydroxyalkoxyalkyl radicals;

aminoalkyl radicals, wherein the amine is optionally monosubstituted or disubstituted with a radical chosen from alkyl radicals, acetyl radicals and hydroxyalkyl radicals;

hydroxy radicals aminoalkyl radicals;

carboxyl radicals;

carboxyalkyl radicals;

carbamoyl radicals;

carbamoylalkyl radicals;

alkoxycarbonyl radicals;

monoalkylaminocarbonyl radicals;

dialkylaminocarbonyl radicals;

monoalkylaminocarbonylalkyl radicals; and dialkylaminocarbonylalkyl radicals;

m ranges from 0 to 4, wherein when m is greater than 1, each R$_4$ may be identical or different; and X$^-$ is a counterion wherein the at least one paraphenylenediamine is not 4-(4-nitrophenyl)-1,1-dimethylpiperazin-1-ium.

26. A composition for dyeing keratin fibres, comprising, in a cosmetic medium that is suitable for dyeing, (a) at least one para-phenylenediamine derivative chosen from formula (Ia), formula (Ib), and their addition salts:

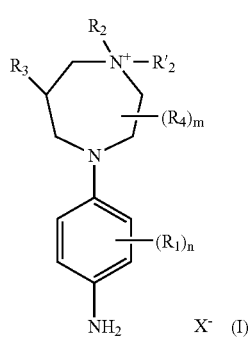

(Ia)

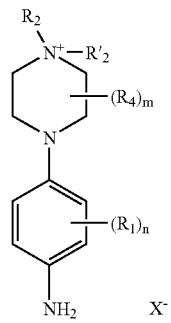

(Ib)

wherein:

R$_1$ is chosen from:

a halogen atom; and saturated and unsaturated C$_1$–C$_8$ aliphatic and alicyclic hydrocarbon-based chains, wherein at least one carbon atom is optionally replaced with at least one entity chosen from oxygen, nitrogen, silicon, sulphur, and SO$_2$ groups; and wherein R$_1$ does not comprise peroxide bonds or diazo, nitro or nitroso radicals;

n ranges from 0 to 4, wherein, when n is greater than 1, each R$_1$ may be identical or different;

R$_2$ and R'$_2$, which may be identical or different, are chosen from:

saturated and unsaturated alkyl radicals, wherein saturated and unsaturated alkyl radicals may optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and —CH$_2$R radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;

aryl radicals; and benzyl radicals;

R$_3$ is chosen from:

a hydrogen atom;

optionally unsaturated alkyl radicals;

hydroxyl radicals;

hydroxyalkyl radicals;

alkoxy radicals;

alkoxyalkyl radicals;

alkylcarbonyl radicals;

hydroxyalkoxyalkyl radicals;

amino radicals, wherein the amine is optionally monosubstituted or disubstituted with a radical chosen from alkyl radicals, acetyl radicals and hydroxyalkyl radicals;

alkyl radicals substituted with at least one hydroxy radical and at least one amino radical;

monoalkylamino radicals;

dialkylamino radicals;

aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion and
(b) at least one adjuvant chosen from anionic, cationic, nonionic, amphoteric and zwitterionic surfactants and mixtures thereof, anionic, cationic, nonionic, amphoteric and zwitterionic polymers and mixtures thereof, inorganic and organic thickeners, antioxidants, penetration agents, sequestering agents, fragrances, buffers, dispersing agents, packaging agents, film-forming agents, ceramides, preserving agents and opacifiers.

27. A composition for dyeing keratin fibres, comprising, in a cosmetic medium that is suitable for dyeing,
(a) at least one para-phenylenediamine derivative chosen from formula (Ia), formula (Ib), and their addition salts:

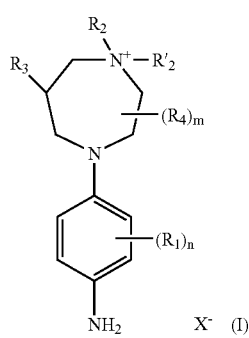

(Ia)

-continued

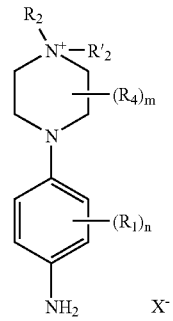

(Ib)

wherein:
$R_1$ is chosen from:
a halogen atom; and
saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;
n ranges from 0 to 4, wherein, when n is greater than 1, each $R_1$ may be identical or different;
$R_2$ and $R'_2$, which may be identical or different, are chosen from:
saturated and unsaturated alkyl radicals, wherein saturated and unsaturated alkyl radicals may optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and
—$CH_2R$ radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;
aryl radicals; and
benzyl radicals;
$R_3$ is chosen from:
a hydrogen atom;
optionally unsaturated alkyl radicals;
hydroxyl radicals;
hydroxyalkyl radicals;
alkoxy radicals;
alkoxyalkyl radicals;
alkylcarbonyl radicals;
hydroxyalkoxyalkyl radicals;
amino radicals, wherein the amine is optionally monosubstituted or disubstituted with a radical chosen from alkyl radicals, acetyl radicals and hydroxyalkyl radicals;
alkyl radicals substituted with at least one hydroxy radical and at least one amino radical;
monoalkylamino radicals;
dialkylamino radicals;

aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;

$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion and
(b) at least one adjuvant chosen from anionic, cationic, nonionic, amphoteric and zwitterionic surfactants and mixtures thereof, anionic, cationic, nonionic, amphoteric and zwitterionic polymers and mixtures thereof.

28. A composition for dyeing keratin fibres, comprising, in a cosmetic medium that is suitable for dyeing, at least one para-phenylenediamine derivative chosen from formula (Ia), formula (Ib), and their addition salts:

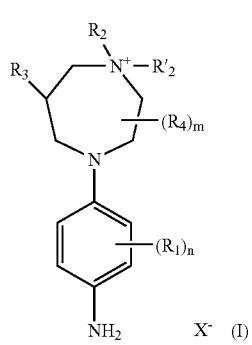
(Ia)

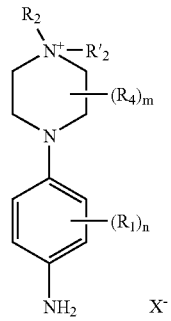
(Ib)

wherein:
$R_1$ is chosen from:
a halogen atom; and
saturated and unsaturated $C_1$–$C_8$ aliphatic and alicyclic hydrocarbon-based chains, wherein at least one carbon atom is optionally replaced with at least one entity chosen from oxygen, nitrogen, silicon, sulphur, and $SO_2$ groups; and wherein $R_1$ does not comprise peroxide bonds or diazo, nitro or nitroso radicals;
n ranges from 0 to 4, wherein, when n is greater than 1, each $R_1$ may be identical or different;
$R_2$ and $R'_2$, which may be identical or different, are chosen from:
saturated and unsaturated alkyl radicals, wherein saturated and unsaturated alkyl radicals may optionally be substituted with at least one radical chosen from carboxyls, alkylcarbonyls, alkoxycarbonyls, carbamoyls, monoalkylcarbamoyls and dialkylcarbamoyls, and saturated and unsaturated heterocyclic radicals comprising 4, 5, 6 or 7 atoms, wherein at least one hetero atom is chosen from nitrogen, oxygen, and sulphur; and
—$CH_2R$ radicals, wherein R is chosen from saturated and unsaturated alkyl radicals, substituted with at least one radical chosen from hydroxyls, alkoxys, thiols, halogens, aminos, monoalkylaminos, dialkylaminos and amino radicals with the amine substituted with a radical chosen from alkylcarbonyls, carbamyls and alkylsulphonyls;
aryl radicals; and
benzyl radicals;
$R_3$ is chosen from:
a hydrogen atom;
optionally unsaturated alkyl radicals;
hydroxyl radicals;
hydroxyalkyl radicals;
alkoxy radicals;
alkoxyalkyl radicals;
alkylcarbonyl radicals;
hydroxyalkoxyalkyl radicals;
amino radicals, wherein the amine is optionally monosubstituted or disubstituted with a radical chosen from alkyl radicals, acetyl radicals and hydroxyalkyl radicals;
alkyl radicals substituted with at least one hydroxy radical and at least one amino radical;
monoalkylamino radicals;
dialkylamino radicals;

aminoalkyl radicals, wherein the amine is optionally monosubstituted or disubstituted with a radical chosen from alkyl radicals, acetyl radicals and hydroxyalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
$R_4$ is chosen from:
saturated and unsaturated alkyl radicals;
hydroxyalkyl radicals;
alkoxyalkyl radicals;
alkylcarbonyl radicals;
hydroxyalkoxyalkyl radicals;
aminoalkyl radicals, wherein the amine is optionally monosubstituted or disubstituted with a radical chosen from alkyl radicals, acetyl radicals and hydroxyalkyl radicals;
hydroxy radicals
aminoalkyl radicals;
carboxyl radicals;
carboxyalkyl radicals;
carbamoyl radicals;
carbamoylalkyl radicals;
alkoxycarbonyl radicals;
monoalkylaminocarbonyl radicals;
dialkylaminocarbonyl radicals;
monoalkylaminocarbonylalkyl radicals; and
dialkylaminocarbonylalkyl radicals;
m ranges from 0 to 4, wherein when m is greater than 1, each $R_4$ may be identical or different; and
$X^-$ is a counterion
wherein the para-phenylenediamine derivative is not substituted with a diazacyclohexane ring wherein n is equal to 0, m is equal to 0 and $R_2$ and $R'_2$ are methyl radicals.

* * * * *